United States Patent [19]

Heaton

[11] Patent Number: 4,973,568

[45] Date of Patent: Nov. 27, 1990

[54] PREPARATION OF A CATALYST USEFUL IN THE DIMERIZATION OF BUTADIENE

[75] Inventor: Duane E. Heaton, Lake Jackson, Tex.

[73] Assignee: The Dow Chemical Company, Midland, Mich.

[21] Appl. No.: 348,625

[22] Filed: May 8, 1989

[51] Int. Cl.$^5$ .................... B01J 21/18; B01J 31/20; B01J 31/18

[52] U.S. Cl. .................... 502/174; 502/200; 502/161; 423/365; 423/417

[58] Field of Search .................... 502/174, 161, 200; 423/365

[56] References Cited

U.S. PATENT DOCUMENTS

| | | | |
|---|---|---|---|
| 2,473,993 | 6/1949 | Gresham et al. | 502/161 |
| 2,572,563 | 10/1951 | Hillyer et al. | 260/344 |
| 2,623,912 | 12/1952 | Smith | 260/668 |
| 2,658,017 | 11/1953 | Marhofer | 167/30 |
| 2,720,509 | 10/1955 | Dees | 260/79 |
| 2,750,352 | 6/1956 | Fanning et al. | 260/45.5 |
| 2,792,419 | 5/1957 | Smith | 260/523 |
| 2,842,526 | 7/1958 | Smith et al. | 260/79.7 |
| 3,143,487 | 8/1964 | Warner | 204/158 |
| 3,146,271 | 8/1964 | Louthan | 260/607 |
| 3,377,397 | 4/1968 | Maxfield | 260/666 |
| 3,412,001 | 11/1968 | Edwards | 204/162 |
| 3,413,355 | 11/1968 | Louthan | 260/609 |
| 3,484,355 | 12/1969 | Warner | 204/162 |
| 3,506,626 | 4/1970 | Warner | 260/79 |
| 3,510,533 | 5/1970 | Maxfield | 260/666 |
| 3,567,608 | 3/1971 | Warner | 204/162 |
| 3,954,665 | 5/1976 | Tkatchenko | 502/161 |
| 4,006,168 | 2/1977 | Kerr | 502/38 |
| 4,234,454 | 11/1980 | Strope | 502/162 |
| 4,238,301 | 12/1980 | Petit | 204/59 R |

Primary Examiner—Chung K. Pak

[57] ABSTRACT

Catalysts suitable for the dimerization of a diolefin, e.g. butadiene to 4-vinylcyclohexene, are prepared by reacting (1) iron chloride and sodium nitrite or alternatively (2) iron nitrosyl chloride with (3) carbon monoxide in an organic solvent in the presence of a readily oxidizable metal, e.g. tin. The catalyst solution is filtered prior to use to remove particulate matter such as unreacted tin.

While the reaction employing iron chloride and sodium nitrite is preferred, the catalyst produced by either method contains a minimum of reducing agent and by-products. It can be isolated and stored in the absence of the butadiene monomer while retaining its stability and activity.

21 Claims, No Drawings

4,973,568

PREPARATION OF A CATALYST USEFUL IN THE DIMERIZATION OF BUTADIENE

BACKGROUND OF THE INVENTION

The complex, iron nitrosyl carbonyl [Fe(NO)$_2$(CO)$_2$], is known to dimerize butadiene to produce vinyl cyclohexene (VCH). It is believed that the catalytic activity is due to the Fe(NO)$_2$ fragment. The methods known to prepare this complex require the reduction of [Fe(NO$_2$)$_2$Cl]$_2$ or the reaction of nitric oxide (NO) on a mixture of iron and FeCl$_3$ in an electrolytic cell and in the presence of butadiene. The iron nitrosyl catalyst is believed to be produced in situ and used therein to obtain the dimerization. Reference to these methods is found in U.S. Pat. No. 4,238,301. Another patent, U.S. Pat. No. 4,234,454, discloses the preparation of various metal nitrosyl catalytic solutions by employing the combination of manganese, zinc or tin together with iron, cobalt or nickel nitrosyl halides to produce the respective metal nitrosyls in a system for dimerizing various conjugated dienes. An earlier patent, U.S. Pat. No. 3,510,533, discloses the dimerization of conjugated dienes with n-allyldinitrosyliron complexes and a method for their preparation. Several methods are given involving the reduction of a $\mu,\mu'$-dihalotetranitrosyldiiron.

The methods of reduction known to the art have numerous disadvantages. Some of these are: (1) the reduction of the metal nitrosyl compound is required to be in the presence of the butadiene, (2) many of the reducing agents themselves will polymerize the butadiene, (3) contaminants are introduced by the reducing agents and (4) catalyst solutions cannot be stored and expected to retain their activity. The dimerized products of the process of the invention may be useful in themselves or as intermediates to other products. Thus, for example, 4-VCH can be (1) chlorinated to make an insecticide, (2) oxidized to make benzoic acid, (3) reacted with hydrogen sulfide in the presence of acid-type catalysts to make sulfur-containing resins and (4) reacted with hydrogen sulfide in the presence of ultraviolet light to make a $\beta$-mercaptoethyl cyclohexane.

SUMMARY OF THE INVENTION

A catalyst suitable for the dimerization of a diolefin, e.g. butadiene to 4-VCH, is prepared by reducing iron nitrosyl chloride with a readily oxidizable metal, e.g. tin, in an organic solvent in the presence of carbon monoxide. The catalyst is believed to be an iron nitrosyl carbonyl. The catalyst performs equally well as other iron nitrosyl catalyst systems. Analogous cobalt and nickel compounds will produce the analogous catalysts, but are not as active as the iron species.

Alternatively and preferably, the catalyst is prepared by reacting FeCl$_2$ and NaNO$_2$ with carbon monoxide in a solvent in the presence of a readily oxidizable metal. The catalyst contains a minimum of reducing agent and by-products. The catalyst thus produced can be isolated and stored in the absence of the butadiene monomer while retaining stability and activity.

DETAILED DESCRIPTION OF THE INVENTION

In general, the catalysts of this invention are suitable for dimerizing to cyclic products the class of conjugated diolefins. While butadiene is exemplified to make 4-VCH, other conjugated dienes can be cyclized similarly. Thus, isoprene and other conjugated diolefins can be dimerized to cyclic compounds.

While ferrous chloride is the preferred compound to be employed in forming the complex used in the catalyst of the invention, other compounds are useful in preparing the catalysts. Thus, for example, [Fe(NO)$_2$Cl]$_2$, FeCl$_3$ and the like are useful for the preparation. Analogous compounds of cobalt and nickel are useful in preparing the analogous catalysts, but such catalysts are not as active as the iron catalysts.

Other reducing agents besides tin which are useful include zinc, manganese, magnesium and the like, or an electrolytic cell may be used in the reduction.

Organic solvents which may be used include ethers, such as diethyl and dibutyl ethers, tetrahydrofuran (THF), diethyleneglycol methyl ether (diglyme), ethyleneglycol methyl ether (monoglyme) and the like; organic esters such as propylene carbonate, ethylene carbonate and ethyl acetate; and nitriles such as acetonitrile and benzonitrile.

Pressures employed for the reaction are those sufficient to maintain carbon monoxide in the organic solution, e.g. from about one to about 1,000 psig.

Temperatures which can be used are those within the range of from ambient to about 250° C., preferably from about 25° to 100° C.

The time of reaction will vary with the amounts of material present and with the pressure and temperature. Generally a time of from about one to 48 hours is operable, but a time of no longer than about 24 hours is usually sufficient to complete the reaction.

The conditions for the dimerization of butadiene are well known to the art and operable with the catalysts of the present invention. The temperature range is from about 20° to about 175° C.; the pressure range is from about atmospheric to about 1,000 psig. and the reaction is conducted for a period of time of from about 10 minutes to about 24 hours.

The following examples are representative of the catalyst preparation and its use:

EXAMPLE 1 Catalyst Preparation

Into a 20 mL autoclave is placed 15.00 g of a 5% solution of [Fe(NO)$_2$Cl]$_2$ in tetrahydrofuran (THF) and 1.12 g of tin powder. The reactor is then flushed with CO (to remove air) and pressured to 75 psig while the contents is stirred. The reactor is maintained at about 25° C. with stirring for about five hours, after which time the reactor is vented and the solution filtered to remove insoluble matter, e.g. tin or tin compounds.

EXAMPLE A (comparative)

The procedure of Example 1 is repeated except that nitrogen is substituted for CO gas, all other parameters remaining the same.

EXAMPLE B (comparative)

Into a 300 mL autoclave is placed 10.12 g of 5% solution of [Fe(NO)$_2$Cl]$_2$ in THF, 45.94 g THF and 1.28 g n-octane*. Tin powder is omitted in this experiment. The reactor is then flushed with CO and pressured to 50 psig, heated to 70° C. and allowed to react for about 5½ hours while stirring. The reactor is then vented.

*The n-octane is used as an analytical standard for gas chromatography.

EXAMPLE 2

In the reactor of Example 1, 1.03 g tin powder is added to 10.0 g of a 5.0 percent solution of [Fe(NO)$_2$Cl]$_2$ in diglyme (diethylene glycol dimethyl ether). The reactor is then flushed with CO gas and pressured to 90 psig while stirring its contents. The temperature is maintained at 25° C. while stirring is continued for 48 hours, after which the reactor is vented and the solution filtered.

EXAMPLE 3

In the same reactor used in Examples 1 and 2 is placed 0.36 g FeCl$_2$, 0.19 g NaNO$_2$, 0.38 g Sn powder and 18.75 g diglyme as solvent. The reactor is then flushed with CO gas and pressured with CO to 75 psig while stirring its contents. The temperature is maintained at 120° C. with continued stirring for 20 hours, after which the reactor is vented and the solution filtered.

EXAMPLE 4

In another experiment propylene carbonate was employed as the solvent using the same reactor as in Examples 1 and 2. The reactant quantities were as follows: 0.37 g FeCl$_2$, 0.20 g NaNO$_2$, 1.19 g Sn powder and 18.0 g propylene carbonate as solvent. The procedure is the same as in Example 3 with the pressure being 90 psig, the temperature 120° C. and the reaction time 14 hours.

The following examples show the use of the catalyst:

EXAMPLE 5 The Dimerization Reaction

The catalyst solution prepared in Example 1 is placed in a 300 mL autoclave to which is added 180 g of butadiene and the reactor is pressured to 300 psi with nitrogen. The reactor is stirred continually and the reaction allowed to continue for a sufficient time to complete the conversion of butadiene, this being determined by sampling at intervals during the reaction. Reaction time for this example is about 14

EXAMPLE 6, 7 AND 8

In the manner of Example 5, the dimerization is carried out using the catalysts prepared in Examples 2, and 4, respectively.

Results obtained using the above catalyst preparations are shown in the following Table:

| Catalyst of Example Number | Conditions/Results | | | |
|---|---|---|---|---|
| | Catalyst[1] (g) | Time (hrs) | Conversion (%) | Selectivity (%) |
| 1 | 10.0 | 15 | 64 | 100 |
| A | 10.0 | 15 | 19 | 100 |
| B | [2] | 14 | 2 | — |
| 2 | 10.0 | 14 | 66 | 100 |
| 3 | 8.0[3] | 14 | 51 | 100 |
| 4 | 10.0 | 14 | 91 | 100 |

[1]The weight used is the weight of the catalyst solution.
[2]The entire amount of catalyst prepared in Example B is used for the dimerization reaction.
[3]Diglyme (34.15 g) is added as diluent to the catalyst.

I claim:

1. A method for making a catalyst suitable for the dimerization of conjugated diolefins which comprises reacting (a) iron, cobalt or nickel chlorides and an alkali metal nitrite or (b) iron, cobalt or nickel nitrosyl chlorides with (c) carbon monoxide in a solvent therefor and in the presence of a readily oxidizable metal.

2. The method of claim 1 wherein the oxidizable metal is selected from the group consisting of tin, zinc, manganese and magnesium.

3. The method of claim 2 wherein the solvent for the reaction is an organic solvent.

4. The method of claim 3 wherein the organic solvent is an organic ether.

5. The method of claim 4 wherein the organic ether is a cyclic ether.

6. The method of claim 5 wherein the cyclic ether is tetrahydrofuran.

7. The method of claim 4 wherein the organic ether is a glycol ether.

8. The method of claim 7 wherein the glycol ether is an alkyl ether of ethylene or diethylene glycol.

9. The method of claim 8 wherein the alkyl ether is methyl or ethyl.

10. The method of claim 9 wherein the methyl ether is the dimethyl ether of ethylene glycol.

11. The method of claim 9 wherein the methyl ether is the dimethyl ether of diethylene glycol.

12. The method of claim 3 wherein the organic solvent is an organic ester.

13. The method of claim 12 wherein the organic ester is an alkylene carbonate.

14. The method of claim 13 wherein the alkylene carbonate is propylene carbonate.

15. The method of claim 3 wherein the organic solvent is an organic nitrile.

16. The method of claim 15 wherein the organic nitrile is acetonitrile.

17. The method of claim 3 wherein the reaction is conducted at a pressure of from about atmospheric to about 1,000 psig.

18. The method of claim 17 wherein the reaction is conducted at a temperature of from about ambient to about 175° C.

19. The method of claim 1 which comprises reacting iron chloride and sodium nitrite with carbon monoxide in an organic solvent in the presence of tin metal.

20. The method of claim 19 wherein the organic solvent is the dimethyl ether of diethylene glycol.

21. The method of claim 19 wherein the organic solvent is propylene carbonate.

* * * * *